(12) United States Patent
Sun et al.

(10) Patent No.: US 12,421,466 B2
(45) Date of Patent: Sep. 23, 2025

(54) PROCESS FOR CONVERSION OF WASTE TO FUEL

(71) Applicant: UCHICAGO ARGONNE, LLC, Chicago, IL (US)

(72) Inventors: Pingping Sun, Downers Grove, IL (US); Theodore R. Krause, Naperville, IL (US); Amgad A. Elgowainy, Lisle, IL (US); Yupo Lin, Naperville, IL (US); Hong Liu, Argonne, IL (US); Hernan Eugenio Delgado de la Garza, Downers Grove, IL (US)

(73) Assignee: UCHICAGO ARGONNE, LLC, Chicago, IL (US)

( * ) Notice: Subject to any disclaimer, the term of this patent is extended or adjusted under 35 U.S.C. 154(b) by 608 days.

(21) Appl. No.: 17/945,839

(22) Filed: Sep. 15, 2022

(65) Prior Publication Data

US 2023/0096521 A1    Mar. 30, 2023

Related U.S. Application Data

(60) Provisional application No. 63/250,721, filed on Sep. 30, 2021.

(51) Int. Cl.
*C10L 1/02* (2006.01)
*C12M 1/00* (2006.01)

(52) U.S. Cl.
CPC ............... *C10L 1/02* (2013.01); *C12M 47/10* (2013.01); *C10L 2200/0476* (2013.01); *C10L 2290/26* (2013.01); *C10L 2290/544* (2013.01)

(58) Field of Classification Search
CPC ............... C10L 1/02; C10L 2200/0476; C10L 2290/26; C10L 2290/544; C12M 47/10;
(Continued)

(56) References Cited

U.S. PATENT DOCUMENTS 6,797,140 B2    9/2004    Lin et al.
2020/0216760 A1    7/2020    Ingolfsson et al.

OTHER PUBLICATIONS

Lanham et al, Medium Chain Carboxylic Acids from Complex Organic Feedstock by Mixed Culture Fermentation (Year: 2019).*

(Continued)

*Primary Examiner* — Randy Boyer
*Assistant Examiner* — Juan C Valencia
(74) *Attorney, Agent, or Firm* — MARSHALL, GERSTEIN & BORUN LLP

(57) ABSTRACT

A method for conversion of food waste to biofuel can include a first fermentation in which food waste is converted $C_2$-$C_4$ short-chain carboxylic acids, and a second fermentation in which the $C_2$-$C_4$ short-chain carboxylic acid are elongated into $C_5$-$C_8$ medium-chain carboxylic acids. Medium-chain carboxylic acids can undergo hydrogenation-dehydration of the medium-chain carboxylic acids into $C_5$-$C_8$ linear olefins. The $C_5$-$C_8$ linear olefins are then oligomerized to a $C_{10}$-$C_{25}$ mixture comprising olefins, paraffin, cycloparaffins, and aromatics through dimerization; and saturated to $C_{10}$-$C_{25}$ mixture by hydrogenation to produce the biofuel.

20 Claims, 3 Drawing Sheets

(58) Field of Classification Search
CPC ...... C12M 21/12; C12M 23/58; C12M 43/02; C10G 3/50; C10G 2400/04; C10G 2400/08; C10G 69/126; C12P 7/40; Y02P 30/20

See application file for complete search history.

(56) References Cited

OTHER PUBLICATIONS

Wei-Cheng Wang, et al, Review of Biojet Fuel Conversion Technologies, NREL/TP-5100-66291, Jul. 2016.

Ryan Davis et al, Process Design and Economics for the Conversion of Lignocellulosic Biomass to Hydrocarbon Fuels and Coproducts: 2018 Biochemical Design Case Update, Technical Report NREL/TP5100-71949, 2018.

Grootscholten et al., 2013. Improving medium chain fatty acid productivity using chain elongation by reducing the hydraulic retention time in an upflow anaerobic filter. Bioresource Technology, vol. 136, (2013) 735-738.

Yeap et al, Selectivity Control during the Single-Step Conversion of Aliphatic Carboxylic Acids to Linear Olefins, ACS Catalysis. 2019, 8, 10769-10773.

Kieth Waldron, Current and emerging separation technologies in biorefining, in "Advances in Biorefineries", woodhead publishing limited, chapter 5, 2014 DOI: 10.1533/9780857097385.1.112.

Yupo J. Lin et al., Bioprocessing of Cost-Competitive Biobased Organic Acids", in "Commercializing Biobased Products: Opportunities, Challenges, Benefits, and Risks, The Royal Society of Chemistry, Green Chemistry series No. 43, Chapter 9, 2016.

\* cited by examiner

PROCESS FOR CONVERSION OF WASTE TO FUEL

CROSS-REFERENCE TO RELATED APPLICATION

The benefit of priority to U.S. Provisional Patent Application No. 63/250,721 filed Sep. 30, 2021 is hereby claimed and the disclosure is incorporated herein by reference in its entirety.

STATEMENT OF GOVERNMENT SUPPORT

The invention was made with support under Contract No. DE-AC02-06CH11357 awarded by the United States Department of Energy to U Chicago Argonne, LLC, operator of Argonne National Laboratory. The government has certain rights in the invention.

BACKGROUND

Development of various process pathways for producing biofuel from biomass feedstocks such as corn stover, sugar cane, beet, plaint oil, algae, is underway using various bio-intermediates as building blocks, such as alcohols (ethanol, butanol), sugars, plant oil, pyrolysis oil, syngas, etc. More recently, the pathway of using building blocks of $C_4$ diol and $C_4$ fatty acid has also been investigated. The minimum fuel selling price (MFSP) for these pathways range from $2.60-$34.7/gal with most pathways having a minimum MFSP of >$4/gal. These pathways face high cost hurdles compared to the petroleum counterpart that has a cost of $3/gallon, largely attributed to the feedstock cost which accounts for about 30-70% of the total production cost, low carbon conversion efficiency that requires more feedstock, as well as process complexity demanding high capital/operation cost.

SUMMARY

There is a need for an improved technology pathway to produce cost-competitive biofuel. Disclosed herein are methods for improved biofuel production from food waste feedstock via integrating fermentation, in-situ electrochemical separation, and catalytic conversion.

A method for conversion of food waste to biofuel in accordance with the disclosure can include a first fermentation in which food waste is converted $C_2$-$C_4$ short-chain carboxylic acids resulting in an aqueous phase comprising the $C_2$-$C_4$ short-chain carboxylic acids; a second fermentation in which, in a fermentation broth comprising the aqueous phase, the $C_2$-$C_4$ short-chain carboxylic acid are elongated into $C_5$-$C_8$ medium-chain carboxylic acids; hydrogenation-dehydration of the medium-chain carboxylic acids into a $C_5$-$C_8$ linear olefins; oligomerizing the $C_5$-$C_8$ linear olefins to $C_{10}$-$C_{25}$ mixture comprising olefins, paraffin, cycloparaffins, and aromatics and aromatics through dimerization; and saturating the $C_{10}$-$C_{25}$ mixture by hydrogenation to produce the biofuel.

DETAILED DESCRIPTION

Figure 1:
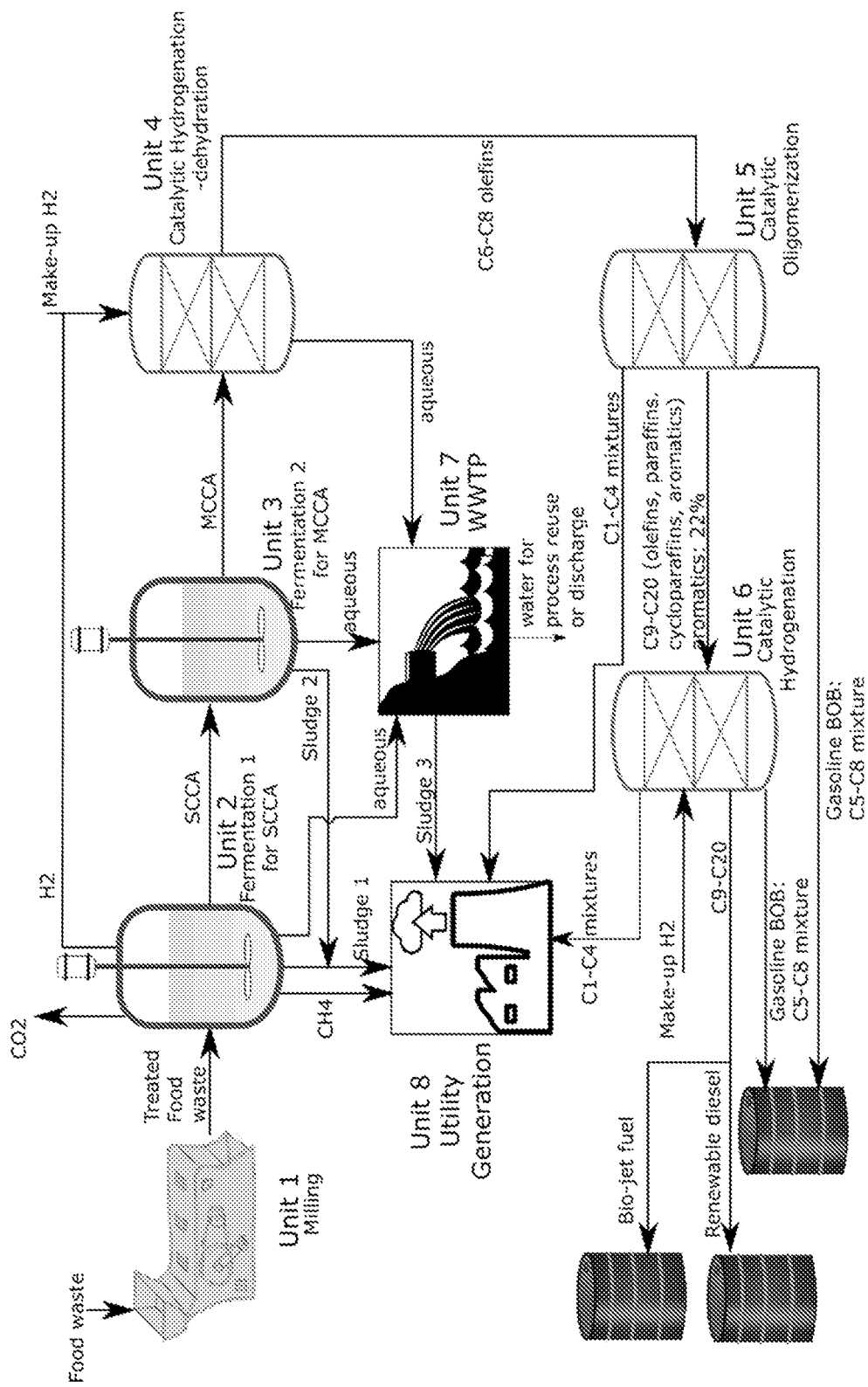
FIG. 1 is an illustration of a process and system in accordance with the disclosure.

Methods of the disclosure include a first fermentation in which food waste is converted to $C_2$-$C_4$ short-chain carboxylic acids; a second fermentation in which the $C_2$-$C_4$ short-chain carboxylic acid are elongated into $C_5$-$C_8$ medium-chain carboxylic acids; and a catalytic process for converting the $C_5$-$C_8$ medium-chain carboxylic acids (MC-CAs) to olefins and ultimately to $C_{10}$-$C_{25}$ hydrocarbons. Units of the disclosure can include first and second fermenters for performing the first and second fermentations, respectively. In embodiments, the first and second fermentation can be performed in a single fermenter.

It has been advantageously found that improve biofuel conversion efficiency can be achieved using medium chain carboxylic acids produced in the methods of the disclosure. Relative to biomass, the resultant MCCA have higher carbon content, energy density, and much higher conversion rate to final products of biofuel. Methods of the disclosure can allow for conversion of food waste to a biofuel at a conversion rate of about 40% to about 64%, which is significantly higher than the conventional process, which reach conversion rates of only up to 30%. Further, methods of the disclosure can produce higher value biofuels, such as jet fuels, and/or improved quality fuels as compared to conventional processes.

As compared to biomass, MCCAs are also more transportable, allowing the biofuel production process to be economically separated by transport of the MCCA to a catalytic conversion facility after fermentation is performed, for example, onsite of the food waste generation. That is, methods of the disclosure can include production of the medium chain carboxylic acids from food waste sources separate from the catalytic conversion of the medium chain carboxylic acids to biofuels. In-line, single site, methods in which food waste streams are converted to the biofuel in a single facility are also contemplated herein.

Food waste can be flowed into the first fermenters for fermenting the food waste to the $C_2$-$C_4$ short-chain carboxylic acids. Any type of food waste stream or organic rich waste water can be used. Reference will be made herein generally to food waste, but should be understood to include any organic rich waste water source. Food waste streams can include, for example, cheese/yogurt production waste or brewery waste. Food waste streams can come from waste generated from food processing industry such as meat, seafood, and/or beverage industries. Beverages industries can include dairy, brewery, soft drink, fruit juice and the like. Additionally or alternatively, food waste can come from household, retail, and/or restaurant food waste. Many food waste streams can consist of already liberated hydrolysates, such as sugars, acids, proteins, and alcohols. The food waste can also contain many non-carbon nutrients, such as N and P. These non-carbon nutrients can be beneficial for bacterial growth in the fermentation stages, which can reduce external nutrient demand. The food waste can be pretreated, for example, by physical and mechanical pretreatment (such as milling, chopping, grinding, freeze-thaw, screw press, lysis-centrifugation, liquid shear/collision and/or high-pressure homogenization), thermal pretreatment (elevated temperatures and/or pressure), chemical pretreatment (such as acid, alkali, ozone, and/or hydrogen peroxide) or a combination of such pretreatment methods.

The first fermentation can include using anaerobic microbiomes (mixed bacterial culture) or specific anaerobic microbial species (e.g. *Lactobacillus bulgaricus, Lactococcus* sp. 1) to convert food waste to SCCAs, such as acetate, propionate, butyrate, lactate, and alcohols such as ethanol, propanol and butanol under pH 4-9 and temperature 15-60° C. with suitable concentrations of nutrients (P, N) and minerals. The first fermentation can result in a conversion efficiency of the food waste to the short-chain carboxylic acids of at least 40%, at least about 50%, at least about 60%, or at least about 70%. Advantageously, the first fermentation can result in a conversion efficiency to short-chain carboxylic acids of up to 85%. After fermentation, phase separation occurs with the produced SCCA (as well as a less amount of unconverted sugars or organics) in aqueous phase (supernatant) and the insoluble impurity and dead biomass (bacteria) in a solid phase (sludge). The aqueous phase can be pumped to the second fermenter. The sludge can be dried and combusted for heat supply. Optionally, a separation can be performed to concentrate the SCCA to increase the feedstock titer for the second fermenter before transferring the aqueous phase to the second fermenter. In this separation, high and purified SCCA titer, e.g., 20-30 wt. % can be economically obtained by, for example, an electrochemical membrane extraction, such as electrodeionization (EDI) from the aqueous phase of first fermenter broth. EDI separation can be used as known in the art, for example, as in S. Data, Y. J. Lin and S. W. Snyder, Current and emerging separation technologies in biorefining, in "Advances in Biorefineries", woodhead publishing limited, chapter 5, 2014 DOI: 10.1533/9780857097385.1.112, and U.S. Pat. No. 6,797,140, the disclosures of which are incorporated herein by reference. Through use of an integrated membrane filtration and extraction, most of the SCCA can be captured and separated from the sludge. Non-charged dissolved byproduct also can be separated from the SCCA titer.

The second fermentation can include using anaerobic microbiomes (mixed bacterial culture) or specific anaerobic microbial species (e.g. *Clostridium kluyveri, Meghsphaera elsdenii, Eubacterium limosum, Eubacterium pyruvativorans*) to convert SCCAs and alcohols to MCCAs under pH 4-9 and temperature 20-60° C. with suitable concentrations of nutrients (P, N) and minerals. The pH can be maintained in the range of 4-9 through addition of any suitable pH adjusting chemical. For example, NaOH can be used to maintain the desired pH. The conversion of short-chain carboxylic acids to the $C_5$-$C_8$ medium-chain carboxylic acids can be at an efficiency of at least 20%, at least 30%, or at least 40%. The MCCAs can then be separated from the fermentation broth with extractants such as amines or phosphine oxides (e.g., trioctylphosphine oxide), which can be pure or mixed with organic solvents like paraffins. In-situ MCCA extraction could also be used to enhance the conversion rate during the second fermentation if low cost, single stage separation can be integrated. In embodiments, the second fermenter can be integrated with any in-situ organic acids extraction technologies, such as solvent extraction, electrochemical separations. For example, an extraction technology such as taught in Yupo J. Lin, Jamie A. Hestekin, Norman Sather, Bioprocessing of Cost-Competitive Biobased Organic Acids", in "Commercializing Biobased Products: Opportunities, Challenges, Benefits, and Risks, The Royal Society of Chemistry, Green Chemistry series No. 43, Chapter 9, 2016 could be used. Integrated fermentation with in-situ, MCCA selective extraction technology, for example, can allow any un-converted SCCAs present in the effluent to be recycled back into the fermenter. The separation can be beneficial in that it can increase the fermentation conversion, reduce toxic impacts of the fatty acids on the microbiome, and/or exclude soluble impurity sourced from the food waste.

Electrochemical membrane extraction, such as electrodeionization (EDI), can also be used to recover sodium hydroxide, or other chemicals used to control pH in the fermentation stages. This can advantageously allow these chemical to be recycled for reuse in the system, which can beneficially reduce the amount of chemical used by the process and system, as well as reduce cost.

Catalytic upgrading is then used to convert the medium-chain carboxylic acids to liquid fuels. The catalytic upgrading process can be tuned depending on the ultimate product to be produced. The product can be a fuel, such as jet, diesel, or gasoline, or a solvent, such as hexane.

A three-step catalytic process can be used, for example. In a first stage, a bifunctional catalyst, such as a $Cu/Al_2O_3$—$SiO_2$ catalyst, can be used to convert the medium-chain carboxylic acids to $C_5$-$C_8$ linear olefins by simultaneous hydrogenation (converting the acids to alcohols) and dehydration (converting alcohol to olefin) reaction. Other hydrogenation or hydrotreating catalysts can include Cu, Pt, Ni, Pd, Co, Ru, CoMo, NiMo, and various bimetallic or trimetallic combinations of the aforementioned elements with other promoting elements (e.g. Zn, Ga, Ir, Re, Cl, etc). Other known catalysts that provide mild hydrogenation such that the hydrocarbons are not converted all the way to alkanes could also be used. Hydrogenation-dehydration can be completed as a two-step process or as a simultaneous process. In the second step of the catalyst process the $C_5$-$C_8$ olefins are oligomerized to form $C_{10}$-$C_{25}$ olefins. A mixture can result including olefins, paraffins, cycloparaffins, and aromatics. The mixture can include a $C_1$-$C_4$ mixture, $C_5$-$C_8$ mixture, and $C_9$-$C_{20}$+ mixture. Aromatics can constitute about 22% or less of the mixture. Conventional olefin oligomerization processes can be used for the dimerization. The resultant $C_{12}$-$C_{16}$ hydrocarbons are then catalytically hydrogenated to saturate olefinic and aromatic content to improve fuel quality in the third step of the catalytic process.

Referring to FIG. 1, a process chart for methods of the disclosure is shown. As illustrated in FIG. 1, food waste can be pre-processed, for example by milling (Unit 1), and then introduced into a first fermenter (Unit 2) for the first fermentation. During the first fermentation, the food waste is converted to short-chain carboxylic acids. Carbon dioxide and $H_2$ can be produced as by-products of the first fermentation. $CO_2$ can be off-gassed. The $H_2$ can be collected and used in downstream processes, for example, in the catalytic hydrogenation-dehydration process. The first fermentation can also result in sludge and methane, which can be removed from the fermenter and combusted to supply heat, steam or for power generation. Conditions can be controlled in embodiments to reduce or avoid the production of methane. An aqueous byproduct also produced in the fermenter can be either reprocessed or disposed of.

The short-chain carboxylic acids produced in the first fermentation are also separated and then introduced into a second fermenter (Unit 3) for the second fermentation. The second fermentation converts the short-chain carboxylic acids to the medium-chain carboxylic acids. The byproducts of the second fermentation can include an aqueous byproduct, which can either be re-processed or disposed of, and a sludge, which can be combusted to generate heat and steam or to generate power. The medium-chain carboxylic acids are separated and introduced into a reaction unit for catalytic hydrogenation-dehydration. As described herein, the medium chain carboxylic acids can be separated continuously in situ during the second fermentation or ex-situ. Any known extraction methods can be used. In situ methods can include, but are not limited to solvent extraction with amines or phosphine oxides (or other types of solvents) and electrochemical separation. Ex-situ methods can include, for example, using a distillation column. Among the in-situ separations technologies, the electrochemical separations can provide potentially low processing cost by using the electric force to manipulate the pH of fermentation broth.

In embodiments, the process can be run as a continuous process in which food waste is continuously introduced into the first fermenter and the resulting aqueous phase (containing short chain carboxylic acids (and alcohols)) are continuously introduced into the second fermenter and the medium chain carboxylic acids are separated in situ.

The medium chain carboxylic acids are introduced into Unit 4. Catalytic hydrogenation-dehydration convers the medium chain carboxylic acids to $C_5$-$C_8$ olefins. A bifunctional catalyst can be used to simultaneously convert the carboxylic acids to alcohols and the alcohols to olefins. A solvent (e.g. paraffins) can be co-fed to dilute the feedstock to maintain an overall high selectivity toward olefins and prevent its conversion into esters, such as hexyl hexanoate.

The $C_5$-$C_8$ olefins are the introduced into Unit 5 for catalytic oligomerization in which the $C_5$-$C_8$ olefins are oligomerized to $C_{10}$-$C_{25}$ olefins. The oligomerization process can be up to 99% efficient. Any mixtures of lower carbon paraffins/olefins can be separated and either collected or combusted to supply heat and steam, or generate power onsite in the system. For example, the oligomerization process can result in a mixture of $C_1$-$C_4$ paraffins/olefins, $C_5$-$C_8$ olefins, and $C_9$-$C_{25}$ olefins, paraffins, cycloparaffins and aromatics. The $C_1$-$C_4$ paraffins/olefins can be separated and used for combustion to supply heat and steam, or generate power onsite. Through distillation, the $C_5$-$C_8$ olefins can be separated and collected for use as gasoline blendstock or naphtha, or be hydrogenated to produce paraffin solvent, and the $C_9$-$C_{25}$ mixture can be introduced in a catalytic hydrogenation unit 6 for conversion of higher value products, such as jet and diesel fuels.

In Unit 6, the $C_9$-$C_{25}$ mixture of olefins, paraffins, and aromatics undergo hydrogenation to produce saturated $C_9$-$C_{25}$ hydrocarbons which can be used, for example, as jet and diesel fuels. Unit 6 can also result in mixtures of lower hydrocarbons, such as $C_1$-$C_4$ hydrocarbons, which can be recycled into the system for power generation and $C_5$-$C_8$ mixtures which can be separate and collected for gasoline blendstock, naphtha or solvent upon additional purification or hydrogenation (hydrotreating).

EXAMPLE

Figure 2:
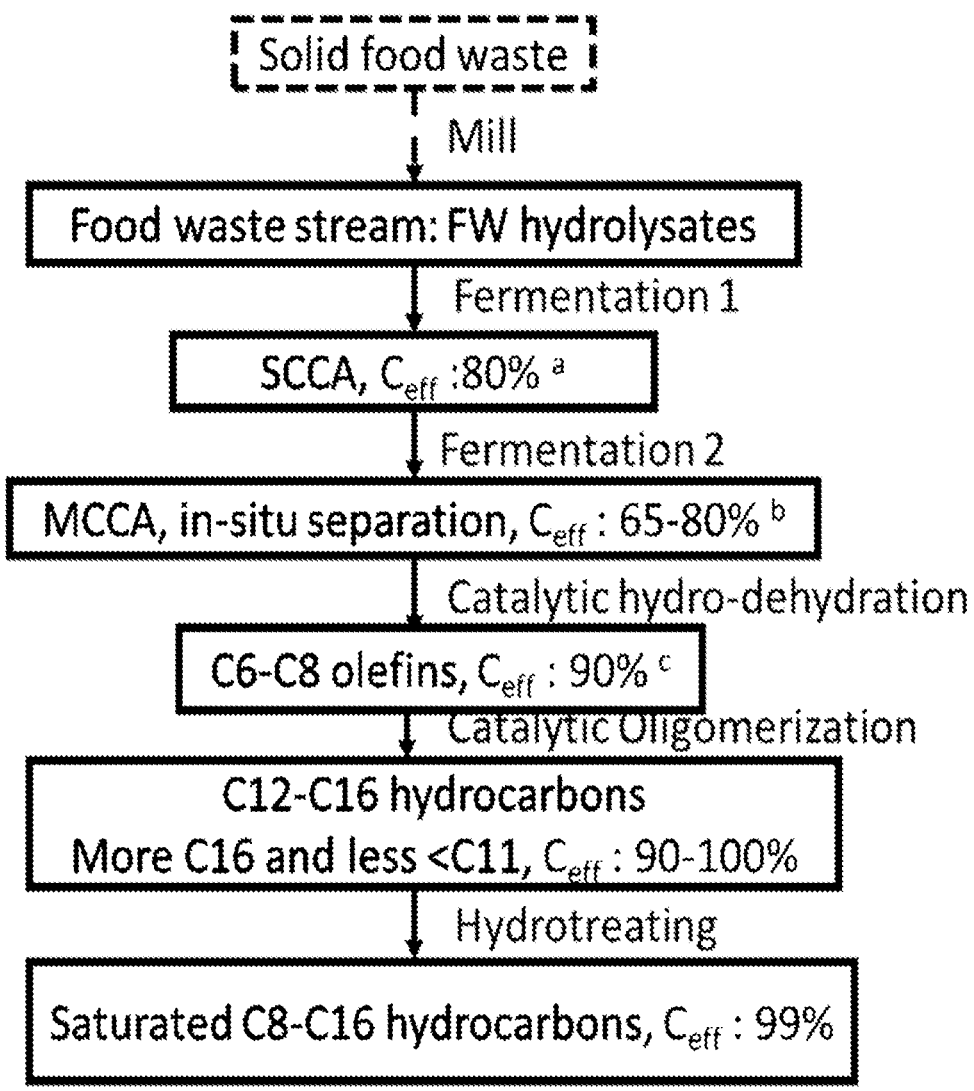
FIG. 2 is a process chart of a process in accordance with the disclosure.

Referring to FIG. 2, a process in accordance with the disclosure was run to convert solid food waste to saturated $C_5$-$C_{16}$ hydrocarbons. The food waste stream tested included acid whey. The food waste stream was processed in a first fermentation to produce short-chain carboxylic acids. The first fermentation was conducted in continuous stirred-tank reactor with a volume ~2 liter at pH of 5.7 and temperature of 36° C. The reactor was operated in batch-fed mode for 13 hours. The lab bacterial culture was enriched from a sludge collected at a local anaerobic digester facility. The conversion efficiency to the short-chain carboxylic acids was 81%. The resulting short-chain carboxylic acids were fed to a second fermentation in which they were converted to the medium-chain carboxylic acids. The second fermentation was conducted in an upflow anaerobic bioreactor with a volume of ~1.5 liter at pH of 6.5 and temperature of 30° C. The reactor was operated in batch mode for 53 hours with liquid recirculation to increase the mixing. The lab bacterial culture was enriched from a sludge collected at a local anaerobic digester facility. The conversion efficiency to medium-chain carboxylic acids was about 33%. Catalytic hydrogenation-dehydration was performed with $Cu/Al_2O_3$—$SiO_2$ as a catalyst to convert the medium-chain carboxylic acids to $C_5$-$C_8$ olefins. The medium-chain carboxylic acids were diluted to 10% in n-dodecane, and the conversion efficiency for medium-chain carboxylic acids was about 83%, with 84% being converted to olefins, and 16% to alkanes. The remaining MCCA and n-dodecane were recovered by distillation and recycled, leading to a global MCCA conversion of 99.9%. The $C_5$-$C_8$ olefins were further converted in the oligomerization step, reaching 95% conversion. The step generated jet and diesel range ($C_{10}$-$C_{25}$) hydrocarbons as well as some lighter hydrocarbons resultant from various reactions, such as dimerization trimerization, cracking, isomerization, ring closing reaction, etc. This reaction was performed in a heterogeneous catalytic reactor with MOGD-2 (as a catalyst, a temperature of 240° C., and a pressure of 6.8 MPa. The resulting hydrocarbons were then hydrotreated to saturate and form saturated $C_8$-$C_{25}$ hydrocarbons (e.g. paraffins, cycloparaffins) at 99% conversion efficiency. The overall system process carbon efficiency (from waste stream to final fuel products) was about 25%, which is comparable to other processes. Further, it is anticipated that additional increase in conversion efficiency would be achieved if the SCCA in the effluent is recycled back into the second fermentation. With such recycling it is believe that an efficiency up to 60% could be achieved, which is significantly higher than the comparative process. The process of the disclosure was able to produce higher value products such as jet fuels and diesel with high quality (high cetane number and low smoke point due to low aromatic content due to hydrogenation, and high heating values due to the presence of cycloparaffins formed by hydrogenating aromatics) as compared to the comparative produces.

COMPARATIVE EXAMPLE

Figure 3:
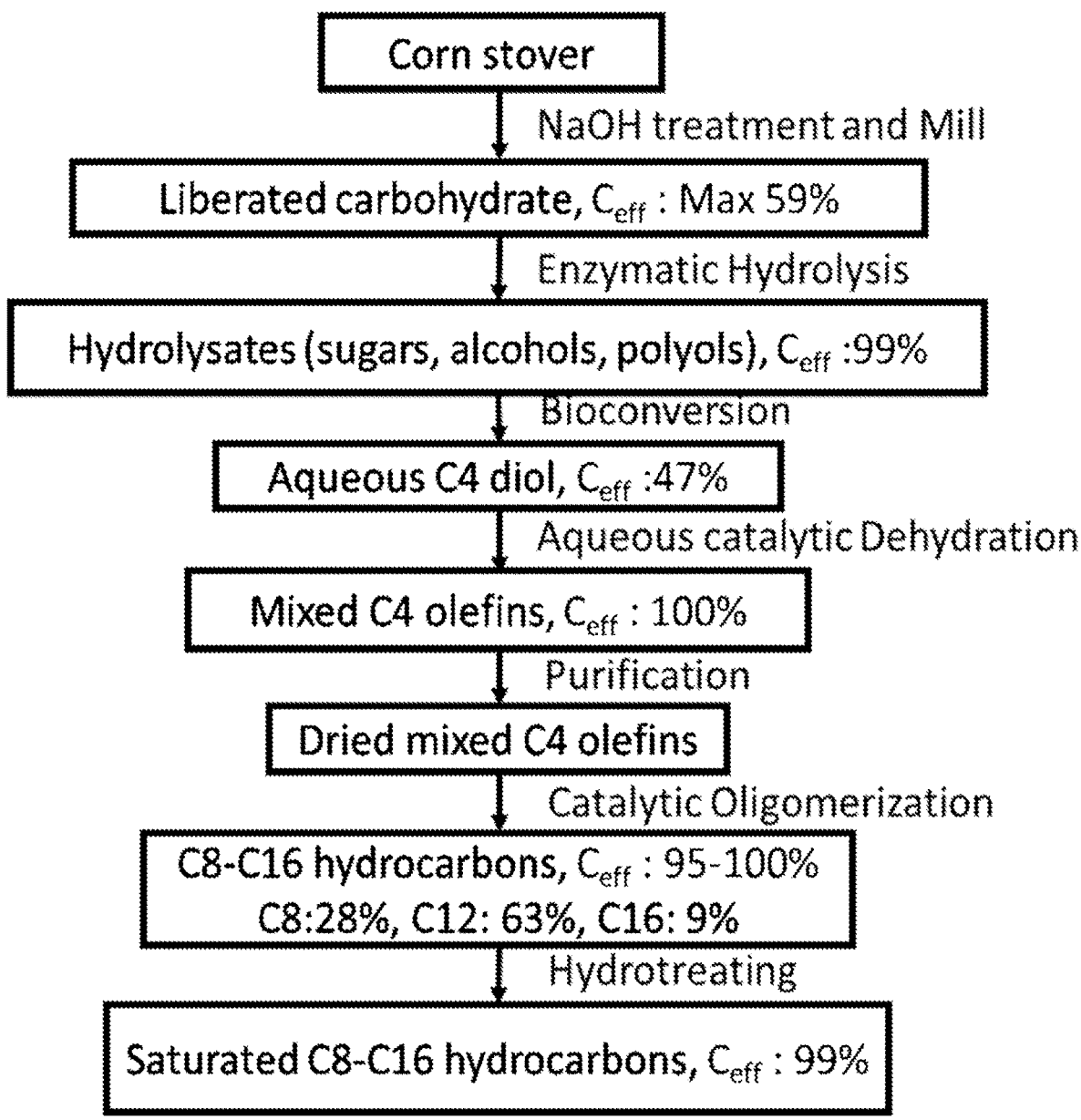
FIG. 3 is a process chart of a conventional process.

A conventional process using the biofuel pathway described in R. Davis et al., *Process Design and Economics for the Conversion of Lignocellulose Biomass to Hydrocarbon Fuels and Coproducts*, Biochemical Design Case Update, Technical Report NREL/TP-5100-71949 (2018) was compared to a process of the disclosure. FIG. 3 illustrates the process. Corn stover was used as the feed stock and treated with NaOH and milled, resulting in liberated carbohydrate. A maximum efficiency of 50% was observed. Enzymatic hydrolysis was used to produce hydrolysates (sugars, alcohols, and polyols) with a conversion efficiency of 99%. Bioconversion was then performed to produce aqueous $C_4$ diol with a conversion efficiency of 47%. Aqueous catalytic dehydration was performed to generated mixed $C_4$ olefins with a 100% conversion efficiency. The $C_4$ olefins were purified and dried. Catalytic oligomerization was performed to generate $C_8$-$C_{16}$ hydrocarbons at a 95-100% efficiency. A mixture of hydrocarbons was produced with 28% $C_8$, 63% $C_{12}$, and 9% $C_{16}$. The resulting mixture was hydrogenated to produce saturated $C_8$-$C_{16}$ hydrocarbons with a 99% conversion efficiency. The overall conversion efficiency from the corn stover was 26%.

The foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In the case of conflict, the present description, including definitions, will control.

Throughout the specification, where the compounds, compositions, methods, and/or processes are described as including components, steps, or materials, it is contemplated that the compounds, compositions, methods, and/or processes can also comprise, consist essentially of, or consist of any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

What is claimed:

1. A method for conversion of food waste to biofuel, comprising:
   a first fermentation in which food waste is converted to $C_2$-$C_4$ short-chain carboxylic acids resulting in an aqueous phase comprising the $C_2$-$C_4$ short-chain carboxylic acids;
   a second fermentation in which in a fermentation broth comprising the aqueous phase, the $C_2$-$C_4$ short-chain carboxylic acid are elongated into $C_5$-$C_8$ medium-chain carboxylic acids;
   hydrogenation-dehydration of the medium-chain carboxylic acids into a $C_5$-$C_8$ linear olefins;
   oligomerizing the $C_5$-$C_8$ linear olefins to a $C_{10}$-$C_{25}$ mixture comprising $C_{10}$-$C_{25}$ olefins, $C_{10}$-$C_{25}$ paraffins, $C_{10}$-$C_{25}$ cycloparaffins, and $C_{10}$-$C_{25}$ aromatics through dimerization; and
   saturating the $C_{10}$-$C_{25}$ mixture by hydrogenation to produce the biofuel.

2. The method of claim 1, wherein the second fermentation is a continuous fermentation and the $C_5$-$C_8$ medium chain carboxylic acids are separated from the fermentation broth in situ.

3. The method of claim 2, wherein the $C_5$-$C_8$ medium chain carboxylic acids are separated from the fermentation broth in situ by solvent extraction or electrochemical separations.

4. The method of claim 1, wherein the $C_5$-$C_8$ medium chain carboxylic acids are separated from the fermentation broth ex situ.

5. The method of claim 1, wherein the biofuel comprises jet fuel.

6. The method of claim 1, wherein the biofuel comprises diesel fuel.

7. The method of claim 1, wherein the biofuel comprises both jet fuel and diesel fuel.

8. The method of claim 1, wherein the yield of the first fermentation is 70-85% $C_2$-$C_4$ short-chain carboxylic acid.

9. The method of claim 1, wherein the catalyst for hydrogenation and dehydrogenation comprises $Cu/Al_2O_3$—$SiO_2$ or Cu/acidic support material.

10. The method of claim 1, wherein hydrogen is produced during the first fermentation and the method comprises flowing the hydrogen for use in the catalytic hydrogenation-dehydration of the medium-chain carboxylic acids.

11. The method of claim 1, wherein the catalytic oligomerization produces a mixture of olefins, paraffins, cycloparaffins, and aromatics.

12. The method of claim 11, wherein the aromatics comprises about 22% of the mixture.

13. The method of claim 11, wherein the mixture comprises $C_1$-$C_4$ olefins, $C_1$-$C_4$ paraffins, and/or $C_1$-$C_4$ unsaturated hydrocarbons, the method further comprising removing $C_1$-$C_4$ olefins, $C_1$-$C_4$ paraffins, and/or $C_1$-$C_4$ other unsaturated hydrocarbons and using the removed $C_1$-$C_4$ olefins, $C_1$-$C_4$ paraffins, and/or $C_1$-$C_4$ other unsaturated hydrocarbons to combust to generate heat, steam or generate power.

14. The method of claim 1, wherein the first and second fermentations are performed in first and second fermenters.

15. The method of claim 1, wherein the first and second fermentations are performed in the same fermenter.

16. The method of claim 1, comprising performing an electrochemical membrane extraction on the aqueous phase to concentration the $C_2$-$C_4$ short-chain carboxylic acids in the aqueous phase.

17. The method of claim 1, comprising maintain pH during the second fermentation in a range of 4-9.

18. The method of claim 17, wherein maintaining the pH during the second fermentation comprises adding a pH adjusting chemical during the second fermentation.

19. The method of claim 18, wherein the pH adjusting chemical is NaOH.

20. The method of claim 18, further comprising performing an electrochemical membrane extraction on the fermentation broth of the second fermentation after separating the $C_5$-$C_8$ medium chain carboxylic acids to further separate the pH adjusting chemical from the fermentation broth.

* * * * *